(12) United States Patent
Rohde et al.

(10) Patent No.: US 7,211,689 B2
(45) Date of Patent: May 1, 2007

(54) METHOD FOR PRODUCTION OF ISOCYANATES

(75) Inventors: Thorsten Rohde, Mannheim (DE); Armin Stamm, Nieder-Olm (DE); Jochem Henkelmann, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 433 days.

(21) Appl. No.: 10/493,498

(22) PCT Filed: Oct. 17, 2002

(86) PCT No.: PCT/EP02/11624

§ 371 (c)(1),
(2), (4) Date: Apr. 22, 2004

(87) PCT Pub. No.: WO03/042170

PCT Pub. Date: May 22, 2003

(65) Prior Publication Data

US 2004/0267047 A1    Dec. 30, 2004

(30) Foreign Application Priority Data

Oct. 23, 2001  (DE) ................ 101 52 118

(51) Int. Cl.
*C07C 263/10* (2006.01)
*C07C 263/00* (2006.01)

(52) U.S. Cl. ..................... 560/347; 560/338

(58) Field of Classification Search ......... 560/330, 560/336, 338, 347
See application file for complete search history.

(56) References Cited

U.S. PATENT DOCUMENTS

| 3,371,114 A | 2/1968 | Sayigh et al. |
| 3,440,268 A | 4/1969 | Stamm |
| 3,484,466 A | 12/1969 | Sayigh et al. |
| 3,492,331 A | 1/1970 | Sayigh et al. |
| 4,888,125 A | 12/1989 | Koenig et al. |

FOREIGN PATENT DOCUMENTS

| CS | 262 295 | | 6/1989 |
| GB | 1359428 | * | 7/1974 |
| WO | 01/17951 | | 3/2001 |

OTHER PUBLICATIONS

Ullmann's Encyclopedia of Industrial Chemistry, 6th Ed, 2000 Electronic release chapter "Isocyanates, Organic- Production".
H. Ulrich, Chemistry & Technology of Isocyanates, Wiley & Sons, 1996, pp. 328-330.

* cited by examiner

*Primary Examiner*—Karl Puttlitz
(74) *Attorney, Agent, or Firm*—Novak Druce & Quigg LLP

(57) ABSTRACT

In a process for preparing isocyanates by reacting the corresponding primary amines with phosgene in an inert solvent, use is made of from 0.01 to 50 mol % of a sulfonamide, based on the total amount of primary amine and isocyanate formed in the reaction solution.

9 Claims, No Drawings

METHOD FOR PRODUCTION OF ISOCYANATES

This application is filed under 35 USC 371 and claims the benefit of PCT/EP02/11624, filed Oct. 17, 2002.

The present invention relates to an improved process for preparing isocyanates by reacting the corresponding primary amines with phosgene in an inert solvent.

Isocyanates are large-scale industrial products having many uses in the field of polyurethane polymers. However, some isocyanates are also employed in the preparation of pharmaceutically active compounds.

The synthesis of isocyanates by reaction of amines with phosgene has been known for a long time. Two basic processes are described in the literature, of which one is carried out at atmospheric pressure and the other is carried out under superatmospheric pressure. The phosgenation under superatmospheric pressure has the disadvantage that it requires a greatly increased outlay in terms of apparatus to cope with the increased safety risk, namely the escape of phosgene.

A process for preparing sulfonyl isocyanates at atmospheric pressure, in which a solution of a sulfonyl amide and an isocyanate as catalyst is reacted with phosgene in an inert solvent, is known from U.S. Pat. No. 3,371,114 and U.S. Pat. No. 3,484,466. In this process, the corresponding sulfonylurea is formed as an intermediate and reacts with phosgene to form the desired sulfonyl isocyanate.

Alkyl and aryl isocyanates are usually prepared from the corresponding amines in two stages at atmospheric pressure by the phosgenation processes described, for example, in Ullmann's Encyclopedia of Industrial Chemistry, 6$^{th}$ edition, 2000 electronic release, Chapter "ISOCYANATES, ORGANIC—Production". In the first stage, the cold phosgenation, the amine is reacted with an excess of phosgene in highly dilute solution and reacted at low temperatures to form the corresponding carbamoyl chloride from which the isocyanate is formed in the second stage at elevated temperature, viz. the hot phosgenation. Owing to their increased basicity compared to aromatic amines, aliphatic and cycloaliphatic primary amines are more difficult to phosgenate and lead to increased formation of by-products. Disadvantages of these processes are the need to carry out the phosgenation in two stages and also, in particular, the formation of an intermediate suspension of sparingly soluble carbamoyl chloride and amine hydrochloride which in turn makes increased dilution of the reaction medium necessary to prevent deposits on and blockages of plant components. Owing to the solid formed, this process cannot be carried out continuously at atmospheric pressure. Furthermore, the process results in formation of a symmetrically N,N'-disubstituted urea as by-product, and the formation of this can only be suppressed at the cost of drastically reduced space-time yields.

Aliphatic and cycloaliphatic amines are frequently used in the form of their salts in the cold/hot phosgenation. However, these salts are sparingly soluble in the reaction medium, so that additional reaction steps and very long reaction times become necessary.

Furthermore, U.S. Pat. No. 3,440,268 and U.S. Pat. No. 3,492,331 teach the reaction of primary amines with phosgene in the presence of an N,N-disubstituted formamide, an N-alkyllactam, an N,N-disubstituted N'-arylformamidine or an N,N,N',N'-tetrasubstituted N"-arylguanidine as catalyst. H. Ulrich, Chemistry & Technology of Isocyanates, Wiley & Sons, 1996, pages 328 to 330, discloses the reaction of primary amines with phosgene in the presence of tertiary amines, tetramethylurea and carbonyldiimidazole as catalyst, and CS 262 295 discloses the use of N,N'-diazabicyclo [2.2.2]octane as catalyst. Some of the compounds specified have to be used in equimolar amounts and form sparingly soluble salts in the form of the catalyst hydrochloride adducts under the reaction conditions. Furthermore, the amine used and the hydrogen chloride formed react to produce sparingly soluble amine hydrochloride.

WO 01/17951 teaches the preparation of isocyanates by phosgenation of the corresponding primary amines in the presence of a monoisocyanate which is initially charged in an inert solvent prior to commencement of the reaction and is admixed with phosgene. A disadvantage of this process is that the preferred low molecular weight aliphatic isocyanates are toxic and require strict safety precautions.

It is an object of the present invention to find a process for preparing isocyanates which no longer has the above-mentioned disadvantages, can be carried out both continuously and batchwise, displays no formation or only insignificant formation of sparingly soluble components, can be carried out without a highly toxic catalyst, makes it possible for the reaction to be carried out in only one reaction stage and leads to a high conversion, a high selectivity and a high space-time yield even under mild temperature and pressure conditions.

We have found that this object is achieved by a process for preparing isocyanates by reacting the corresponding primary amines with phosgene in an inert solvent, wherein from 0.01 to 50 mol % of a sulfonamide, based on the total amount of primary amine and isocyanate formed in the reaction solution, is used.

The sulfonamide which can be used in the process of the present invention has the formula (I)

$$R^1\!-\!SO_2\!-\!NH_2 \qquad\qquad (I),$$

where the radical $R^1$ is a carbon-containing organic radical.

For the purpose of the present invention, a carbon-containing organic radical is an unsubstituted or substituted, aliphatic, aromatic or araliphatic radical. This may contain one or more heteroatoms such as oxygen, nitrogen, sulfur or phosphorus, for example —O—, —S—, —NR—, —CO—, —N=, —SiR$_2$—, —PR— and/or —PR$_2$, and/or be substituted by one or more functional groups which contain, for example, oxygen, nitrogen, sulfur and/or halogen, for example by fluorine, chlorine, bromine, iodine and/or a cyano group (the radical R is likewise a carbon-containing organic radical). The carbon-containing organic radical can be a monovalent radical or else a divalent or trivalent radical.

The radical $R^1$ is preferably
  an unbranched or branched, acyclic or cyclic, unsubstituted or substituted alkyl radical which has from 1 to 30 aliphatic carbon atoms and in which one or more of the CH$_2$ groups may be replaced by heteroatoms such as —O— or —S— or by heteroatom-containing groups such as —CO—, —NR— or —SiR$_2$—, and in which one or more of the hydrogen atoms may be replaced by substituents such as aryl groups or functional groups; or
  an unsubstituted or substituted aromatic radical which has from 3 to 30 carbon atoms and one ring or two or three fused rings and in which one or more ring atoms may be replaced by heteroatoms such as nitrogen and in which one or more of the hydrogen atoms may be replaced by substituents such as alkyl or aryl groups or functional groups.

Particular preference is given to using sulfonamides (I) whose radical $R^1$ is an unbranched or branched $C_1$–$C_{20}$-alkyl radical such as methyl, ethyl, 1-propyl, 2-propyl (sec-propyl), 1-butyl, 2-butyl (sec-butyl), 2-methyl-1-propyl (isobutyl), 2-methyl-2-propyl (tert-butyl), 1-pentyl, 2-pentyl, 3-pentyl, 2-methyl-2-butyl (tert-amyl), 1-hexyl, 2-hexyl, 3-hexyl, 2-methyl-2-pentyl, 3-methyl-3-pentyl or 2-methoxy-2-propyl;

an unbranched or branched $C_5$–$C_{20}$-cycloalkyl radical such as cyclopentyl, cyclohexyl or cyclooctyl; or a $C_6$–$C_{20}$-aryl or $C_3$–$C_{20}$-heteroaryl radical which may be unsubstituted or substituted by one or more $C_1$–$C_4$-alkyl radicals, for example phenyl, 2-methylphenyl (o-tolyl), 3-methylphenyl (m-tolyl), 4-methylphenyl (p-tolyl), 2,6-dimethylphenyl, 2,4-dimethylphenyl, 2,4,6-trimethylphenyl, 2-methoxyphenyl, 3-methoxyphenyl, 4-methoxyphenyl, 2-pyridyl, 3-pyridyl, 4-pyridyl, 3-pyridazinyl, 4-pyridazinyl, 5-pyridazinyl, 2-pyrimidinyl, 4-pyrimidinyl, 5-pyrimidinyl, 2-pyrazinyl, 2-(1,3,5-triazin)yl, 1-naphthyl, 2-naphthyl, 2-quinolyl, 8-quinolyl, 1-isoquinolyl or 8-isoquinolyl.

Very particular preference is given to using sulfonamides (I) whose radical $R^1$ is an unbranched or branched $C_1$–$C_{10}$-alkyl radical;

an unbranched or branched $C_5$–$C_{10}$-cycloalkyl radical; or a $C_6$–$C_{12}$-aryl radical which may be unsubstituted or substituted by one or more $C_1$–$C_4$-alkyl radicals.

In particular an aromatic sulfonamide, very particularly preferably p-toluenesulfonamide, is used in the process of the present invention.

The sulfonamide is used in a catalytic amount of from 0.01 to 50 mol %, based on the total amount of primary amine and isocyanate formed in the reaction solution. In calculating the total amount of primary amine and isocyanate formed, the molar amounts of the not yet reacted starting material (primary amine) and the product which has been formed (isocyanate) and any intermediates present are to be added. In the process of the present invention, preference is given to using from 0.01 to 25 mol %, particularly preferably from 0.5 to 20 mol % and very particularly preferably from 1 to 15 mol %, of sulfonamide, based on the total amount of primary amine and isocyanate formed in the reaction solution.

In the process of the present invention, the sulfonamide is generally initially charged in an inert solvent. For the purposes of the present invention, inert solvents are solvents which are chemically inert toward the primary amine used, the phosgene, the isocyanate formed and the sulfonamide used. "Chemically inert" means that the diluents do not react chemically with the substances mentioned under the chosen conditions. Preference is given to using aromatic or aliphatic hydrocarbons, particularly preferably monosubstituted or polysubstituted aromatic hydrocarbons such as toluene, o-, m-, p-xylene, ethylbenzene, chlorobenzene or o-, m-, p-dichlorobenzene. Very particular preference is given to o-, m- or p-xylene, chlorobenzene, o-, m-, p-dichlorobenzene and mixtures thereof.

In general, the introduction of phosgene is then commenced. It can be introduced in liquid or gaseous form. It is usual for from about 10 to 50% of the theoretically required amount of phosgene, based on the reaction volume, to be introduced initially.

Addition of the primary amine to the phosgene-laden starting solution of sulfonamide in the inert solvent is then commenced. Further phosgene is introduced in accordance with the progress of the reaction and the amount of amine added.

The primary amines which can be used in the process of the present invention have the formula (II)

$$R^2\text{—}NH_2 \qquad (II),$$

where the radical $R^2$ is a carbon-containing organic radical as defined above.

The radical $R^2$ is preferably an unbranched or branched, acyclic or cyclic, unsubstituted or substituted alkyl radical which has from 1 to 30 aliphatic carbon atoms and in which one or more of the $CH_2$ groups may be replaced by heteroatoms such as —O—, or —S— or by heteroatom-containing groups such as —CO—, —NR— or —SiR$_2$— and in which one or more of the hydrogen atoms may be replaced by substituents such as aryl groups or functional groups, with the exception of —OH, —SH and —COOH groups; or an unsubstituted or substituted aromatic radical which has 3 to 30 carbon atoms and one ring or two or three fused rings and in which one or more ring atoms may be replaced by heteroatoms such as nitrogen and in which one or more of the hydrogen atoms may be replaced by substituents such as alkyl or aryl groups or functional groups, with the exception of —OH, —SH and —COOH groups.

In particular, the radical $R^2$ may bear one or more further $NH_2$ groups, so that oligoamines having two or more $NH_2$ groups are explicitly included as primary amines. The primary amine used is particularly preferably a monoamine having one $NH_2$ group or a diamine having two $NH_2$ groups, each having from 1 to 20 carbon atoms.

As examples of suitable acyclic and substituted or unsubstituted alkyl radicals $R^2$, mention may be made of methyl, ethyl, 1-propyl, 2-propyl (sec-propyl), 1-butyl, 2-butyl (sec-butyl), 2-methyl-1-propyl (isobutyl), 2-methyl-2-propyl (tert-butyl), 1-pentyl, 2-pentyl, 3-pentyl, 2-methyl-2-butyl (tert-amyl), 1-hexyl, 2-hexyl, 3-hexyl, 2-methyl-2-pentyl, 3-methyl-3-pentyl, 1-octyl, 1-decyl, 2-aminoethyl, 3-aminopropyl, 4-aminobutyl, 5-aminopentyl, 6-aminohexyl, 8-aminooctyl, phenylmethyl, 1-phenylethyl, 1-phenylpropyl or 1-phenylbutyl.

As examples of cyclic and substituted or unsubstituted cycloalkyl radicals $R^2$, mention may be made of cyclopentyl, cyclohexyl, cyclooctyl or 3-aminomethyl-3,5,5-trimethylcyclohexyl.

As examples of aromatic and heteroaromatic and substituted or unsubstituted radicals $R^2$, mention may be made of phenyl, o-, m-, p-tolyl and aminotolyls.

It may be emphasized that enantiomerically pure, optically active compounds or mixtures thereof having an optically active carbon bound to the $NH_2$ group can also be used as primary amines. Advantageously, the process of the present invention leads to only a small degree of racemization, generally below 2%, during the reaction and the work-up.

The primary amine used in the process of the present invention is very particularly preferably 1,6-diaminohexane, cyclohexylamine, isophoronediamine (3-aminomethyl-3,5,5-trimethylcyclohexylamine), aniline, a diaminotoluene, diphenylmethane-4,4-diamine, R-(+)- and S(−)-phenylethylamine.

The molar ratio of the total amount of phosgene introduced to the primary amine groups to be phosgenated is generally from 1 to 10, preferably from 1 to 5 and particularly preferably from 1 to 2, in particular from 1.2 to 1.8.

The amount of inert solvent is generally from 100 to 2000% by weight and preferably from 300 to 1000% by weight, based on the total amount of the primary amine present and the isocyanate formed.

The process of the present invention is generally carried out at from 20 to 200° C., preferably from 20 to 150° C. and particularly preferably from 50 to 100° C. In carrying out the process of the present invention, the pressure is generally from 0.05 to 0.5 MPa abs and preferably from 0.08 to 0.12 MPa abs.

After the desired amount of phosgene and amine has been added, the reaction solution obtained is generally left for a certain time, in general from 30 minutes to 6 hours, under the reaction conditions to allow further reaction to occur. To remove or reduce the amount of excess phosgene and its reaction products carbon dioxide and hydrogen chloride from/in the reaction solution, it is usual for inert gas subsequently to be passed through the mixture with intensive mixing ("stripping").

The process of the present invention can in principle be carried out either continuously or batchwise, with continuous operation being preferred. The process can be carried out in any apparatus suitable for a reaction with phosgene. Suitable reactors are, for example, stirred vessels.

The reaction mixture after the reaction is generally worked up by known methods. Preference is given to isolating the desired isocyanate by fractional distillation. The sulfonamide used as catalyst is preferably recovered by distillation and, in the case of a continuous process, recirculated.

In a general embodiment for the batchwise preparation of isocyanates, the sulfonamide together with an inert solvent are placed while stirring in a reactor, for example a stirred vessel, and the solution is loaded with phosgene. The reaction system is then brought to the desired temperature and the introduction of the amine is commenced. Further phosgene is introduced in accordance with the progress of the reaction and the amount of amine fed in. After the desired amount of phosgene has been fed in, the reaction solution is left at the set temperature for some time while continuing to stir to allow further reaction to occur.

During this after-reaction time, phosgene which is still present in the reaction solution reacts with residual amine. To remove or reduce the concentration of the excess phosgene and its reaction products carbon dioxide and hydrogen chloride from/in the reaction solution, it is possible to pass inert gas through the mixture while mixing intensively ("stripping"). The reaction solution obtained is then passed to work-up. In general, the work-up is carried out by distillation, if appropriate under reduced pressure. In the case of relatively high-boiling isocyanates, other purification methods, for example crystallization, are also possible.

In a general embodiment for the continuous preparation of isocyanates, the sulfonamide together with an inert solvent are placed while stirring in the reactor, for example a stirred vessel, and the solution is loaded with phosgene. The reaction system is then brought to the desired temperature and the continuous introduction of the amine is commenced. Further phosgene is introduced continuously in accordance with the progress of the reaction and the amount of amine fed in. After the contents of the reactor have largely reacted to form isocyanate, the amounts of amine and phosgene are adjusted so that both are added essentially in the stoichiometric required ratio. An amount of the reaction solution corresponding to the amount fed in is taken from the reaction apparatus, for example via a level regulator or an overflow. The reaction solution which has been taken off is collected in a downstream container, for example a stirred vessel, to allow further reaction to occur. After the downstream container has been filled by the reaction mixture, the overflow is, if appropriate, freed of the coproducts carbon dioxide and hydrogen chloride by stripping as described above and is passed to work-up. The work-up can be carried out, for example, by distillation.

The process of the present invention makes it possible to prepare isocyanates by continuous or batchwise phosgenation of primary amines. Compared to known, catalyst-free processes, it makes it possible to carry out the actual reaction in only a single reaction stage under mild temperature and pressure conditions, and gives a higher conversion of primary amine, a high selectivity and a high space-time yield of isocyanate. Compared to the known, catalyst-free processes and the known processes in the presence of a catalyst, the process of the present invention has no tendency, or only an insignificant tendency, to form sparingly soluble components. The risk of deposits on and blockages of plant components is significantly reduced thereby, which represents a decisive safety advantage when handling toxic phosgene. Furthermore, the nonformation or only insignificant formation of sparingly soluble components makes it possible to carry out a continuous process for the first time and gives significant advantages in the subsequent work-up.

The sulfonamides used in the process of the present invention are generally nontoxic or have only a low toxicity, which represents, in particular, an advantage over the use of an aliphatic monoisocyanate described in WO 01/17951.

EXAMPLES

Experimental Apparatus

The experimental apparatus comprised a 1 glass vessel provided with a stirrer, a thermostat, an inlet tube for the gaseous phosgene and a two-part condenser cascade. The two-part condenser cascade comprises an intensive condenser which was maintained at −10° C. and a carbon dioxide condenser which was maintained at −78° C. The experiments were carried out at atmospheric pressure.

Comparative Example 1

500 g of chlorobenzene were placed in the glass vessel and 40 g of gaseous phosgene was introduced at room temperature. The reaction mixture was subsequently heated to 77° C., with vigorous phosgene reflux being established. While stirring vigorously at 77–80° C., a total of 99.2 g of cyclohexylamine (1 mol) dissolved in 200 g of chlorobenzene and at the same time a further 92 g of phosgene were introduced over a period of 3 hours. After addition was complete, the system was maintained at 77–80° C. for a further one hour without introduction of phosgene to allow further reaction to occur and the residual unreacted phosgene was subsequently stripped out at 50° C. by means of nitrogen. The reaction mixture obtained was a suspension from which the solid obtained was separated by filtration. 15 g of solid which, according to IR-spectroscopic analysis, was mainly amine hydrochloride were able to be isolated in this way. The filtered crude product was worked up by distillation. Removal of the solvent and fractional distillation gave 88.8 g of cyclohexyl isocyanate (0.710 mol). This corresponds to 71.0% of the theoretical yield.

Example 2

According to the Present Invention 500 g of chlorobenzene and 4.3 g of p-toluenesulfonamide (0.025 mol) were placed in the glass vessel and 33 g of gaseous phosgene was introduced at room temperature. The reaction mixture was subsequently heated to 79° C., with vigorous phosgene reflux being established. While stirring vigorously at 78–81° C., a total of 99.2 g of cyclohexylamine (1 mol) dissolved in 200 g of chlorobenzene and at the same time a further 122 g of phosgene were introduced over a period of 3 hours. After addition was complete, the system was maintained at 78–81° C. for a further one hour without introduction of phosgene to allow further reaction to occur and the residual unreacted phosgene was subsequently stripped out at 50° C. by means of nitrogen. The reaction mixture obtained was a fluid suspension from which the solid obtained was separated by filtration. <0.5 g of solid was able to be isolated in this way. Cyclohexyl isocyanate was worked up by distillation. Removal of the solvent and fractional distillation gave 105.1 g of cyclohexyl isocyanate (0.833 mol). This corresponds to 83.3% of the theoretical yield.

Compared to comparative example 1 without use of a catalyst, example 2 according to the present invention using p-toluenesulfonamide displays only a very small proportion of solids. Thus, only very little solid has to be separated off in the process of the present invention.

The significantly lower proportion of solids enables the process of the present invention to be carried out significantly more simply, more safely and with fewer problems. In particular, the risk of deposits on and blockages of plant components is significantly reduced, which represents a decisive safety advantage when handling toxic phosgene and makes a continuous process possible.

Futhermore, example 2 according to the present invention using p-toluenesulfonamide displays, at a yield of 83.3% of the theoretical yield, a considerably higher conversion than comparative example 1 without the use of a catalyst, where a yield of 71.0% of the theoretical yield is obtained.

Compared to the known processes which have to be carried out batchwise because of solids formation, the ability to carry out a continuous process and to achieve the significantly higher yields enables a significant increase in the space-time yield to be achieved. Unreacted amine can be returned to the reaction apparatus, so that the achievable yield is considerably higher in the process of the present invention than in the known processes.

We claim:

1. A process for preparing isocyanates which comprises reacting the corresponding primary amines with phosgene in an inert solvent in the presence of from 0.01 to 50 mol % of a sulfonamide, based on the total amount of primary amine and isocyanate formed in the reaction solution.

2. A process as claimed in claim 1, wherein the sulfonamide is present in from 0.01 to 25 mol % based on the total amount of primary amine and isocyanate formed in the reaction solution.

3. A process as claimed in claim 1, wherein the sulfonamide is of the formula (I)

$$R^1SO_2NH_2 \qquad (I),$$

where the radical $R^1$ is an unbranched or branched $C_1$–$C_{10}$-alkyl radical, an unbranched or branched $C_5$–$C_{10}$-cycloalkyl radical or a $C_6$–$C_{12}$-aryl radical which may be unsubstituted or substituted by one or more $C_1$–$C_4$-alkyl radicals.

4. A process as claimed in claim 3, wherein the sulfonamide is p-toluenesulfonamide.

5. A process as claimed in claim 1, wherein the primary amine is a monoamine having one $NH_2$ group or a diamine having two $NH_2$ groups, each having from 1 to 20 carbon atoms.

6. A process as claimed in claim 5, wherein the primary amine is 1,6-diaminohexane, cyclohexylamine, isophoronediamine, aniline, a diaminotoluene, diphenylmethane 4,4'-diamine, R-(+)- or S(–)-phenylethylamine.

7. A process as claimed in claim 1, wherein the reaction is carried out at from 20 to 200° C. and a pressure of from 0.05 to 0.5 MPa abs.

8. A process as claimed in claim 1, wherein the inert solvent is used in an amount of from 100 to 2000% by weight, based on the total amount of primary amine present and isocyanate formed.

9. A process as claimed in claim 1, wherein the inert solvent is o-, m- or p-xylene, chlorobenzene, o-, m-, p-dichlorobenzene or a mixture thereof.

\* \* \* \* \*